United States Patent [19]

Jaber et al.

[11] Patent Number: 5,262,967
[45] Date of Patent: Nov. 16, 1993

[54] SYSTEM FOR TESTING AND INSPECTING CONCRETE

[75] Inventors: Tarif M. Jaber, Eden Prairie; Kim A. Pearson, St. Paul, both of Minn.

[73] Assignee: Braun Intertec Engineering, Inc., Minneapolis, Minn.

[21] Appl. No.: 729,566

[22] Filed: Jul. 15, 1991

[51] Int. Cl.$^5$ .......................... G06F 7/46; G06F 15/46
[52] U.S. Cl. .................................. 364/552; 364/550; 356/378
[58] Field of Search ................... 364/550, 551.01, 552; 356/378

[56] References Cited

U.S. PATENT DOCUMENTS

| | | | |
|---|---|---|---|
| 4,693,608 | 9/1987 | Kitagawa et al. | 364/394 |
| 4,943,930 | 7/1990 | Radjy | 364/506 |
| 5,134,575 | 7/1992 | Takagi | 364/552 |

OTHER PUBLICATIONS

Brochure on the Trilogy Systems Model TS 600 Concrete Inspection System, pp. A-15 and A-16.
"Fryer New Product Bulletin—MCS-83", Frank E. Fryer Co.
Letter of quotation from HMP Ltd. re: MCS-87 Computerized Linear Traverse System, Oct. 21, 1987.

*Primary Examiner*—Jack B. Harvey
*Assistant Examiner*—Brian M. Buroker
*Attorney, Agent, or Firm*—Merchant & Gould, Smith, Edell, Welter & Schmidt

[57] ABSTRACT

A system and method for determining the air-void or aggregate content of a concrete specimen according to the point count and modified point count method utilizing coordinate data collected during linear traverse method inspection. A computer operates a computer driven stage containing the concrete specimen under a microscope, whereby positional data is transmitted to the computer. The computer controls the linear traverse pattern of the stage under the microscope, although the operator has the option to manually increase or decrease the traverse rate during the inspection cycle. The computer automatically records linear traverse coordinate data for the entire traverse pattern. An operator records in the computer beginning and ending coordinate data for air-voids or aggregates encountered on the traverse pattern from which the air-void or aggregate content is calculated according to the linear traverse method. The computer then calculates the air-void content according to the point count and modified point count methods using the linear traverse coordinate data and the beginning and ending coordinate data of air-voids recorded by the operator.

6 Claims, 1 Drawing Sheet

SYSTEM FOR TESTING AND INSPECTING CONCRETE

TECHNICAL FIELD OF THE INVENTION

The present invention relates to a system and method for automatically determining the air-void or aggregate content of hardened concrete according to the point count, modified point count and linear traverse methods from coordinate data collected during a single inspection of the specimen. More particularly, coordinate data collected for the linear traverse method inspection is utilized to evaluate the specimen according to the point count and modified point count methods, thereby producing a quantitative and qualitative analysis of air-void and aggregate content in the specimen.

BACKGROUND OF THE INVENTION

Concrete durability in northern climates is greatly dependant on the concrete's ability to maintain its integrity under freeze/thaw cycles. The engineering and concrete industries have established a relationship between concrete durability during temperature cycles and the air-void content of the concrete. Aggregate concentration and distribution is also a factor.

Air-voids are small hollow spaces enclosed in the cement paste of the concrete. Air-voids are generally larger than two micrometers in diameter. The term air-void includes both "entrapped" and "entrained". Entrained air-voids are spherical in shape, while entrapped air-voids are irregularly shaped and often result from improper consolidation. Aggregates are solid material in the concrete, such as stones.

The inspection of air-void content in concrete is usually performed in accordance with the American Society of Testing and Materials (ASTM) standard ASTM C 457-82a, which is entitled, "Standard Practice for Microscopical Determination of Air-Void Content and Parameters of the Air-Void System in Hardened Concrete," which publication is well-known in the art of concrete inspection and to which reference may be made for further details on the methodology and calculation of air-void content analysis with regard to the system of the present invention. The ASTM has established two primary procedures for determining air-void content in hardened concrete. The linear traverse method entails examining microscopically a finely ground section of concrete on a series of regularly spaced lines of traverse. The operator records the beginning and ending coordinates of air-voids and/or aggregates encountered along the traverse lines. This data yields information on the total number of sections of air-voids intersected by the microscope cross hairs, the total distance traversed across sections to voids, the total distance traversed across the remainder of the concrete, and the total distance traversed across the paste and aggregates.

The point count and modified point count methods entail microscopic examination of the concrete section along a similar series of regularly spaced traverse lines. The specimen is moved under the microscope at evenly spaced intervals along the traverse lines. The operator records the frequency at which air-voids or aggregates are encountered.

In the past, examining concrete specimens for their compliance with ASTM C 457 requirements was time consuming, inaccurate and expensive. Typically, the specimen would be attached to a positioning table under a microscope. The operator would record the location of the specimen in relation to the microscope cross hairs at the beginning of a traverse line. The operator would next manually reposition the table until an air-void or aggregate was encountered. Another data point would then be recorded. Again, the operator would reposition the table to the other edge of the air-void and record the position. Repeating this process for over 1,000 data points was extremely tedious and time consuming.

A number of devices are available for accelerating this process. The Trilogy Systems Model TS 600 Concrete Inspection System utilizes a joy stick to position the table containing the specimen. Upon reaching the start of an air-void, the operator presses a computer key for the data point type (i.e., air-voids or aggregates) and to prompt a computer to record the location. The operator then moves the table using the joy stick to the end of the air-void and again presses a button which instructs the computer to record the ending data point for the air-void.

The model MCS-83 computer controlled inspection system from Frank E. Fryer Co. utilizes a computer controlled stage which determines traverse line spacing, traverse length, and the number of points counted, as well as the distance between the points. The operator activates a counter mechanism at the beginning and ending of air-voids. Scanning speed is operator controlled in either manual positioning or automatic mode.

SUMMARY OF THE INVENTION

The present invention relates to a system and method for automatically determining the air-void content of hardened concrete according to the point count and modified point count methods using coordinate data collected while performing linear traverse method inspection. During the linear traverse method inspection, coordinate data of the traverse pattern is collected, as well as data relating to the location of air-voids or aggregates. The data from the linear traverse method inspection is used to calculate the presence or absence of air-voids or aggregates at any point along the traverse pattern, allowing the specimen to be evaluated according to the point count and modified point count methods.

The present invention provides for the simultaneous quantitative and qualitative inspection of air-voids and aggregates in the specimen of hardened concrete, from data collected during a single inspection.

Another aspect of the present invention relates to variable speed controller button which allows the operator to increase or decrease the traverse rate in real-time, depending on the concentration of air-voids or aggregates in the specimen.

The present invention also utilizes the traverse line coordinate data to perform localized analysis of the specimen. Statistical analysis of the specimen can be performed for any subset of the data collected, allowing the operator to identify localized abnormalities.

DESCRIPTION OF THE PREFERRED EMBODIMENT

Figure 1:
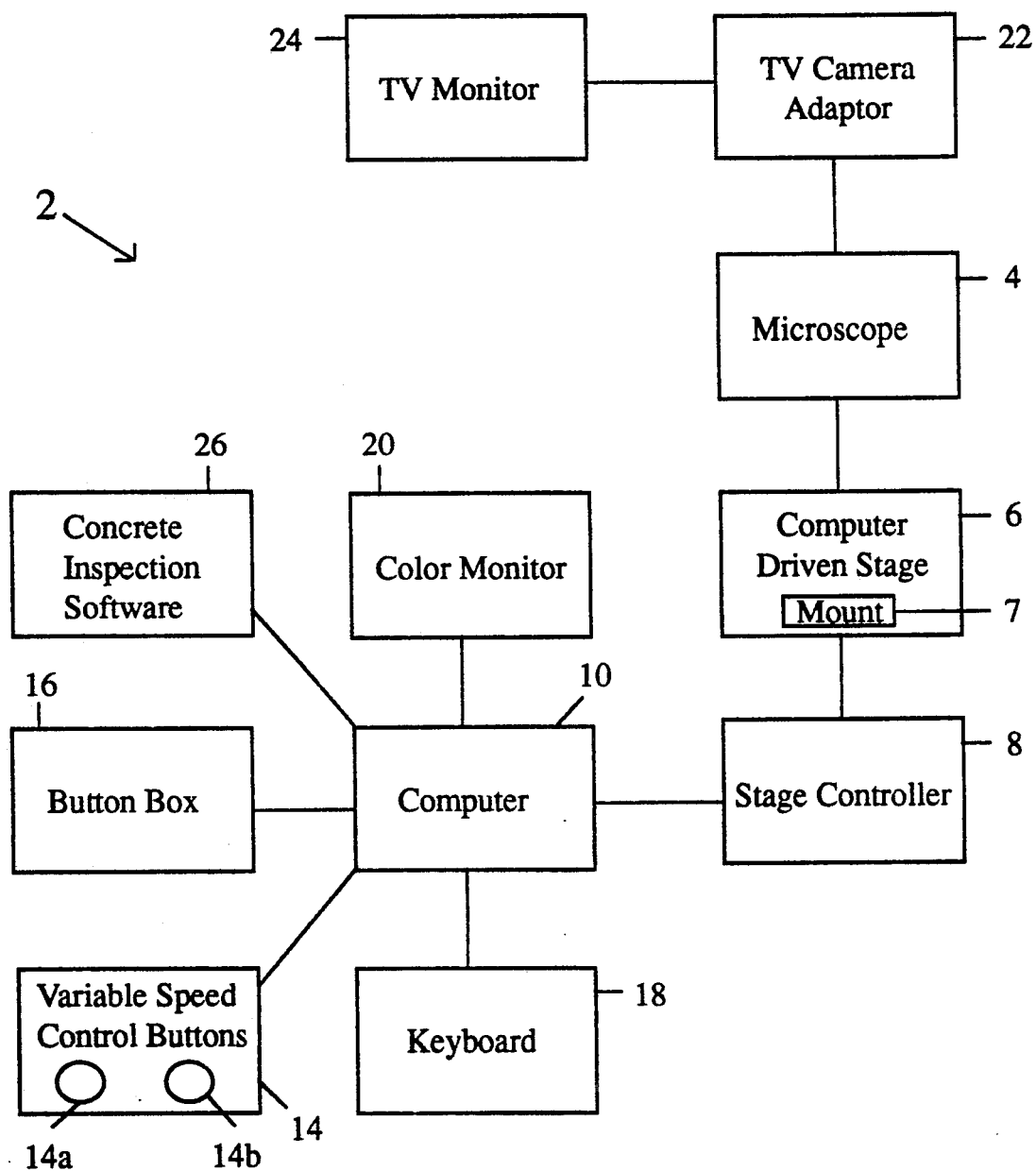
FIG. 1 is a simplified block diagram of the hardware and software of the present invention.

FIG. 1 illustrates the concrete air-void inspection system 2 of the present invention. A microscope 4 with targeting cross hairs is positioned under a computer driven stage 6 with positioning encoders. The output signal from the encoders is transmitted to a stage controller 8 which communicates with a computer 10. The computer 10 uses the signal from the stage controller 8 to control the position of the computer driven stage 6. Mounting apparatus 7 provides for mounting a specimen to the computer-driven stage.

A button box 16 is provided for signaling to the computer 10 when air-voids or aggregates are encountered. The computer driven stage is also positioned manually using the buttons on the button box 16. A keyboard 18 is provided for performing analysis on the collected data. Variable speed control buttons 14a and 14b are connected to the computer to control the rate of motion of the computer driven stage 6 during the traverse cycle. In the preferred embodiment of the present invention, the buttons 14a and 14b are located in physical proximity to the button box 16.

The computer 10 controls the movement of the computer driven stage 6 beneath the microscope 4 in increments of 0.00001 inches. Concrete inspection software 26 receives operator input primarily from the button box 16, which is used to identify the location of air-voids and aggregates.

The system 2 status is displayed on a color monitor 20. In an alternative embodiment, a TV camera adaptor 22 and TV monitor 24 can be attached to the microscope 4 to reduce operator eye-strain.

SPECIMEN PREPARATION

Specimens of hardened concrete are typically obtained by removing core samples from a concrete structure. Multiple specimens of concrete are generally obtained in a given region of the structure.

The surface of the specimen is ground with successively finer abrasives until the surface is suitable for microscopic observation. The surface is then washed and scrubbed to remove grit and loose particles of concrete. The surface is considered satisfactorily prepared when the edges of the air-voids are sharp and not rounded or crumbled.

DATA COLLECTION

ASTM C 457 describes two methods for performing air-void content determination; the linear traverse method and the modified point count method. In both methods, the concrete specimen is placed on the computer driven stage 6 and moved beneath the microscope 4 along evenly spaced traverse lines, with the minimum distance traversed along a line being three inches. The minimum total length to be traversed is based on the maximum size of aggregates in the concrete and ranges from 55" for fine aggregates (3/16") to 160" for coarse aggregates (6").

The specimen may be scanned from left to right or top to bottom. Aggregates, which are large solid matter within the concrete such as stones, may optionally be recorded. Air-voids may also be optionally categorized as being entrained or entrapped. If air-voids are to be categorized, one button on the button box 16 is used to identify entrained air-voids and another button is used to identify entrapped air-voids. Otherwise, a single button is used to identify air-voids of either type.

During data collection, the operator presses predefined buttons on the button box 16 to indicate the presence of air-voids and aggregates in the microscope 4 cross hairs. The functions assigned to each button may be set by the user in the concrete inspection software 26 and saved to a configuration file in the computer 10, allowing the operator to customize the system 2. The button box 16 can also be used to operate the computer driven stage 6 in a manual mode. The manual mode is used primarily to position the specimen prior to data collection. The concrete inspection software 26 can also be configured to emit audible tones indicating which button is being pressed.

LINEAR TRAVERSE METHOD

In the linear traverse method, a specimen is moved continuously beneath the microscope 4 along traverse lines. The concrete inspection software 26 controls the movement of the computer driven stage 6 to traverse a predefined pattern during data collection.

The operator collects data as the microscope 4 targeting cross hairs travel along the traverse lines, by pressing a button on the button box 16 to indicate the presence of air-voids and/or aggregates. The button is pressed when the cross hairs enters the air-void or aggregate and released when the cross hairs exit the air-void void or aggregate.

The variable speed control buttons 14a and 14b allow the operator to increase and decrease the traverse rate, in real-time, during the inspection cycle. For example, as the occurrences of air-voids or aggregates increase, the operator will need to decrease the traverse rate of the computer driven stage 6 to insure accuracy. Conversely, as the occurrences of air-voids or aggregates decrease, the operator can temporarily increase the traverse rate, thereby decreasing the inspection time.

The computer 10 retains coordinate data representing the entire traverse pattern. This allows the operator to abort the traverse cycle at any point and repeat the scan starting at the point where errors may have occurred. If only one segment of the traverse cycle is repeated, the computer 10 will return the computer driven stage 6 to the location where the operator aborted the traverse cycle.

The linear traverse method yields more information about the specimen than the modified point count method. In the linear traverse method, the total number of air-voids and aggregates that have been traversed is known. In addition, the air-void and aggregate chord length that has been traversed can be determined. Finally, as discussed above, the computer 10 records traverse line coordinate data for the entire traverse pattern.

Point Count Method

In the point count method, the specimen is moved from point to point along the same traverse pattern used in the linear traverse method. Data is collected at evenly spaced intervals along these traverse lines. When the computer 10 stops at a particular interval, the operator identifies whether the cross hairs are in an air-void, paste or aggregates by pressing the assigned button on the button box 16. After the point has been identified, the concrete inspection software 26 automatically advances to the next point along the traverse lines. As discussed above in connection with the linear traverse method, the computer retains coordinate data for the traverse lines. This allows the operator to abort the traverse cycle and re-score portions of the specimen if necessary.

Air-void concentration is calculated based on the percentage of the points inspected that were identified as being in air-voids. This technique can also be used to inspect for aggregates or paste. However, the point count method does not evaluate the specimen between inspection points, creating uncertainty regarding the results. For this reason, the modified point count method was developed.

MODIFIED POINT COUNT METHOD

As in the point count method, the specimen is moved from point to point along the same traverse pattern used in the linear traverse method. Data is collected at evenly spaced intervals along these traverse lines by an operator who identifies whether the cross hairs are in an air-void, paste or aggregates by pressing the assigned button on the button box 16. After the point has been identified, the concrete inspection software 26 automatically begins advancing the specimen to the next point along the traverse pattern. However, contrary to the point count method, the operator presses a button on the button box 16 to score the number of air-voids intersected along the traverse pattern between inspection intervals.

As discussed above in connection with the linear traverse method and point count method, the computer retains coordinate data for the traverse lines, allowing the operator to abort the traverse cycle and re-score portions of the specimen if necessary.

Air-void concentration is calculated based on the percentage of the points inspected that were identified as being in air-voids along the traverse pattern. A similar inspection can be performed for aggregates or paste. While the modified point count method can be performed in one third to one-half the time required for the linear traverse method, it does not provide information regarding the chord length traversed.

DATA ANALYSIS

The computer 10 retains coordinate data for the entire traverse pattern covered during the linear traverse method. While the specimen is being traversed, the beginning and ending coordinates of all air-voids and aggregates are recorded by the operator using the button box 16. Based on the above data collected during the linear traverse method, the following values can be calculated; air content, specific surface, spacing factor, percentage of paste, the total count and total chord length of entrained and entrapped bubbles, voids per inch, the frequency count of entrained and entrapped bubbles as a function of size, the average and maximum aggregate size, and the total count and total length of aggregates.

The traverse pattern coordinate data and beginning and ending coordinates for air-voids and aggregates allows the computer 10 to determine the presence or absence of air-voids or aggregates at any point along the traverse pattern. Consequently, the specimen can be analyzed under the point count and modified point count methods utilizing the data collected during the linear traverse method. The operator can compare the results of the linear traverse method with the point count and modified point count methods directly, while actually having performed only the linear traverse method inspection. Data analysis may be either output to the computer monitor or printed on a computer printer.

Finally, the concrete inspection software 26 utilizes the coordinate data for the traverse lines to perform localized analysis of the specimen. The data analysis discussed above can be performed for any subset of the coordinate data. A small region along the traverse pattern can be analyzed, allowing the operator to identify localized abnormalities.

While a particular embodiment has been described, it will be appreciated that modifications can be made without departing from the scope of the invention as defined by the appended claims.

I claim:

1. A system for inspecting a concrete specimen for air-void content according to the modified point count method utilizing coordinate data collected during linear traverse method inspection, comprising:

(a) a computer;
   (b) a microscope with targeting cross hairs;
   (c) a computer driven stage with positioning encoders attached to said computer driven stage, whereby positioning data is transmitted to said computer;
   (d) means of fixing said specimen on said computer driven stage and initializing said specimen to a coordinate system in said computer;
   (e) means for traversing said specimen under said microscope in a linear traverse pattern, whereby linear traverse coordinate data is recorded in said computer;
   (f) means for recording in said computer beginning and ending coordinate data for said air-voids on said traversed specimen;
   (g) means for calculating said air-void content according to said linear traverse method; and
   (h) means for calculating the air-void content according to said modified point count method using said linear traverse coordinate data and said beginning and ending coordinate data of said air-voids.

2. The system for inspecting a concrete specimen for air-void content according to claim 1, further comprising means for calculating the air-void content according to said modified point count method using said linear traverse coordinate data and said beginning and ending coordinate data of aid air-voids for a localized area of said concrete specimen.

3. A system according to claim 1, further including means for calculating the air-void content according to a point count method using said linear traverse-coordinate data and said beginning and ending coordinate data of said air-voids.

4. A system for inspecting a concrete specimen for aggregate content according to the modified point count method utilizing coordinate data collected during linear traverse method inspection, comprising:

(a) a computer;
   (b) a microscope with targeting cross hairs;
   (c) a computer driven stage with positioning encoders attached to said computer driven stage, whereby positioning data is transmitted to said computer;
   (d) means of fixing said specimen on said computer driven stage and initializing said specimen to a coordinate system in said computer;
   (e) means for traversing said specimen under said microscope in a linear traverse pattern, whereby linear traverse coordinate data is recorded in said computer;
   (f) means for recording in said computer beginning and ending coordinate data for said aggregates on said traversed specimen;

(g) means for calculating said aggregate content according to said linear traverse method; and (h) means for calculating the aggregate content according to said modified point count method using said linear traverse coordinate data and said beginning and ending coordinate data of said aggregates.

5. The system for inspecting a concrete specimen for aggregate content according to claim 4, further comprising means for calculating the aggregate content according to said modified point count method using said linear traverse coordinate data and said beginning and ending coordinate data of said aggregates for a localized area of said concrete specimen.

6. A system according to claim 4, further including means for calculating the aggregate content according to a point count method using said linear traverse coordinate data and said beginning and ending coordinate data of said aggregates.

* * * * *